United States Patent
Frenkel et al.

(10) Patent No.: US 11,897,858 B2
(45) Date of Patent: *Feb. 13, 2024

(54) SALT AND SOLID STATE FORMS OF ESCATALOPRAM

(71) Applicant: Mark Hasleton, Raanana (IL)

(72) Inventors: Anton Frenkel, Netanya (IL); Raeann Ruiyun, Montville, NJ (US)

(73) Assignee: Mark Hasleton, Raanana (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/866,513

(22) Filed: Jul. 17, 2022

(65) Prior Publication Data

US 2022/0363655 A1 Nov. 17, 2022

Related U.S. Application Data

(63) Continuation of application No. 16/764,033, filed on May 14, 2020, now Pat. No. 11,390,597, which is a continuation-in-part of application No. PCT/IB2018/057824, filed on Oct. 9, 2018.

(60) Provisional application No. 62/569,755, filed on Oct. 9, 2017.

(51) Int. Cl.
*C07D 307/87* (2006.01)

(52) U.S. Cl.
CPC ........ *C07D 307/87* (2013.01); *C07B 2200/13* (2013.01)

(58) Field of Classification Search
CPC .................. C07D 307/87; C07B 2200/13
USPC ........................................ 514/469
See application file for complete search history.

(56) References Cited

U.S. PATENT DOCUMENTS

| | | |
|---|---|---|
| 4,943,590 A | 7/1990 | Boegesoe et al. |
| 7,723,533 B2 | 5/2010 | Dancer et al. |
| 11,390,597 B2 * | 7/2022 | Frenkel ............... A61P 25/24 |
| 2004/0167209 A1 | 8/2004 | Dancer et al. |
| 2011/0053997 A1 | 3/2011 | Beliaev |

FOREIGN PATENT DOCUMENTS

| | | |
|---|---|---|
| WO | 2004/056791 A1 | 7/2004 |
| WO | 2004/085416 A1 | 10/2004 |

OTHER PUBLICATIONS

Celexa (citalopram) label approved by US FDA Jul. 1998.
Celexa (citalopram) label approved by US FDA Jan. 2017.
Luo Y, et al., "National Prescription Patterns of Antidepressants in the Treatment of Adults With Major Depression in the US Between 1996 and 2015: A Population Representative Survey Based Analysis", Frontiers in Psychiatry 11(35) Feb. 14, 2020.
Berge et al., "Pharmaceutical Salts", J. Pharmaceutical Sciences, 66(1) pp. 1-19, Jan. 1977.
Lexapro (escitalopram oxalate), label approved by US FDA Aug. 2002.
Lexapro (escitalopram oxalate), label approved by US FDA Jan. 2017.
Dancer et al., "Attempted Resolution of Citalopram Using (−)-O,O'-Di-p-toluoyl (R,R)-tartaric Acid, and Reflections on an Alkylation Reaction; Comment on an Article by Elati et al.", Organic Process Research & Development 2009, vol. 13, No. 1, pp. 23-33.
Stahl and Nakano, "Pharmaceutical Aspects of the Drug Salt Form", pp. 83-116 in "Handbook of pharmaceutical salts: properties, selection, and use", Wiley-VCH 2002.
Zoloft (sertraline), label approved by US FDA Jun. 2017.
Paxil (paroxetine), label approved by US FDA Jan. 2017.
Prozac (fluoxetine), label approved by US FDA Mar. 2017.
Elati, CR, et al. "Substrate Modification Approach to Achieve Efficient Resolution: Didesmethylcitalopram: A Key Intermediate for Escitalopram." Organic Process Research & Development, vol. 11, No. 2, pp. 289-292, 2007.

* cited by examiner

*Primary Examiner* — Kristin A Vajda

(74) *Attorney, Agent, or Firm* — Daniel Feigelson

(57) ABSTRACT

The present disclosure relates to a new salt of escitalopram and its solid state forms, processes for the preparation thereof, pharmaceutical compositions thereof, and methods of use thereof.

20 Claims, 2 Drawing Sheets

SALT AND SOLID STATE FORMS OF ESCATALOPRAM

CROSS-REFERENCE TO RELATED APPLICATION

This application is a continuation of U.S. Ser. No. 16/764,033, which is § 371 of PCT/IB2018/057824, and claims the benefit of U.S. Ser. No. 62/569,755, filed Oct. 9, 2017. The disclosures of the aforesaid patent applications are incorporated by reference herein.

TECHNICAL FIELD

The present invention relates to a new salt of escitalopram, namely escitalopram gentisate, and its solid state forms, processes for the preparation thereof, pharmaceutical compositions thereof, and methods of use thereof.

BACKGROUND

Escitalopram

Escitalopram, (S)-1-(3-dimethylaminopropyl)-1-(4-fluorophenyl)-1,3-dihydro-2-benzofuran-5-carbonitrile), has the following formula:

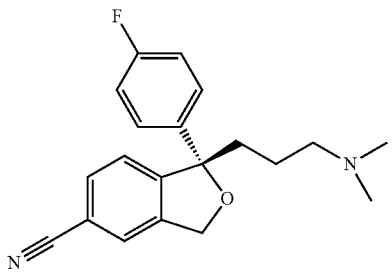 [SMILES: CN(C)CCC[C@@]1(c2ccc(F)cc2)OCc2cc(C#N)ccc21]

Escitalopram oxalate is a selective serotonin (5-HT) reuptake inhibitor (SSRI), developed by Lundbeck for the treatment of major depressive disorder (MDD), generalized anxiety disorder (GAD), panic disorders, social phobias and obsessive-compulsive disorder. The drug is approved by the U.S. Food and Drug Administration for the treatment of adults and children over 12 years of age with major depressive disorder (MDD) or generalized anxiety disorder (GAD), and for additional indications in other countries worldwide. Escitalopram oxalate is commercially available in both oral tablets and oral solution dosage forms, and traded under the brand names Lexapro® and Cipralex®. Since 2011, the drug has been available as a generic in most major markets. The escitalopram pamoate salt is also commercially available as an active pharmaceutical ingredient.

Escitalopram is the eutomer of citalopram, and, along with its oxalate and pamoate salts, was described in EP347066. Despite being known for more than 30 years, only a few other salt forms of the drug have been recorded. US20040167209 discloses escitalopram hydrobromide and amorphous escitalopram tartrate. Elati et al (2007) discloses escitalopram (−) di-p-toluoyltartrate. U.S. Pat. No. 7,723,533 discloses escitalopram crystalline free base.

Active Pharmaceutical Ingredient (API) Salt Selection

Different salts of an API may possess different properties. Such variations in the properties of different salts may provide a basis for improving formulation, for example, by facilitating better processing or handling characteristics, improving the dissolution profile, or improving stability and shelf-life. These variations in the properties of different salts may also provide improvements to the final dosage form, for instance, if they serve to improve bioavailability. Different salts of an API may also give rise to a variety of polymorphs, which may in turn provide additional opportunities for providing an improved drug substance and product.

Polymorphism, the occurrence of different crystal forms, is a property of some molecules and molecular complexes. A single compound, like escitalopram, may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD) pattern, infrared absorption fingerprint, Raman absorption fingerprint, and solid state (13C-) NMR spectrum. One or more of these techniques may be used to distinguish different polymorphic forms of a compound.

New salts and solid state forms and solvates of a drug substance can provide advantageous properties, such as ease of handling, ease of processing, storage stability, and ease of purification, or as desirable intermediate crystal forms that facilitate conversion to other salts or polymorphic forms. New polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life. For at least these reasons, there is a need for additional salt and solid state forms of escitalopram.

SUMMARY OF THE INVENTION

The present invention relates to escitalopram gentisate, and solid state forms thereof. In a preferred embodiment, the present invention relates to escitalopram gentisate Form I. In another preferred embodiment, the present invention relates to escitalopram gentisate Form II.

The present invention further encompasses the use of the above described salt and solid state forms thereof, for the preparation of other solid state forms of escitalopram gentisate, other escitalopram salts and their solid state forms thereof.

The present invention further encompasses compositions comprising escitalopram gentisate, and solid state forms thereof, and their preparation. In some embodiments, the composition is a pharmaceutical composition.

The present invention further encompasses pharmaceutical compositions comprising escitalopram gentisate, and solid state forms thereof, and their preparation.

In one embodiment, the present invention encompasses processes for preparing said pharmaceutical formulation comprising combining escitalopram gentisate and solid state forms thereof, and at least one pharmaceutically acceptable excipient.

The salt and solid state forms of escitalopram gentisate defined herein as well as the pharmaceutical compositions and formulations thereof can be used as medicaments, preferably for the treatment of neuropsychiatric disorders, including major depressive disorder (MDD) and generalized anxiety disorder (GAD). A preferred embodiment of the invention, comprises administering a therapeutically effective amount of escitalopram gentisate to a subject suffering from a neuropsychiatric disorder, more preferably, to a subject suffering from major depressive disorder (MDD) or generalized anxiety disorder (GAD) or otherwise in need of treatment.

DETAILED DESCRIPTION OF ILLUSTRATIVE EMBODIMENTS

Figure 1:
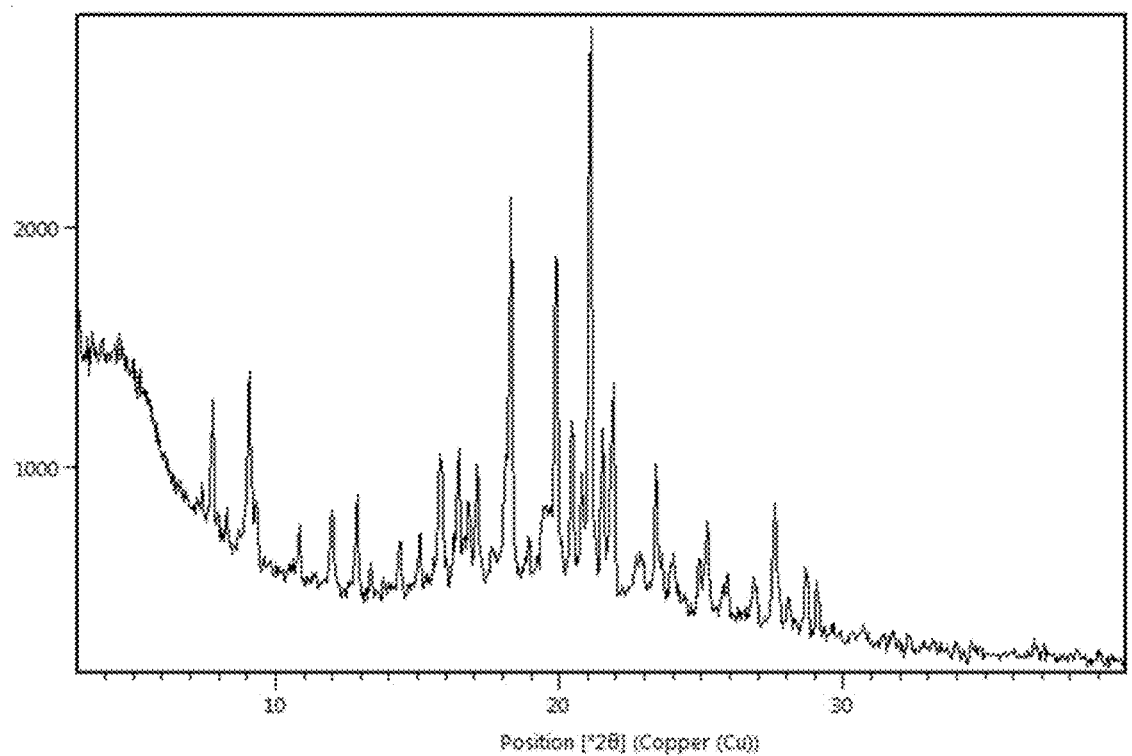
FIG. 1 shows an X-ray powder diffraction (XRPD) pattern of Form I of escitalopram gentisate prepared according to Example 3.

As used herein, escitalopram gentisate means escitalopram gentisate salt.

As used herein, a crystal form or a crystalline form may be referred to as being characterized by graphical data "as depicted in" a Figure. Such data include, for example, powder X-ray diffractograms. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

Escitalopram gentisate, or crystal forms of escitalopram gentisate as referred to herein, as being characterized by graphical data "as depicted in" a Figure, will thus be understood to include any crystal form of escitalopram gentisate, characterized with the graphical data having such small variations, as are well known to the skilled person, in comparison with the Figure.

As used herein, unless stated otherwise, XRPD peaks reported herein are preferably measured using CuKα radiation, λ=1.5418 Å, preferably, XRPD peaks reported herein are measured using CuK α radiation, λ=1.5418 Å, at a temperature of 25±3° C.

A process or step may be referred to herein as being carried out "overnight." This refers to a time interval, e.g., for the process or step, that spans the time during the night, when that process or step may not be actively observed. This time interval is from about 8 to about 20 hours, or about 10 to about 18 hours, typically about 16 hours.

As used herein, and unless stated otherwise, the term "anhydrous" in relation to escitalopram gentisate salt, a crystalline escitalopram gentisate salt or a solid state form thereof, which does not include any crystalline water (or other solvents) in a defined/nondefined, stoichiometric/non-stoichiometric amount within the crystal. Moreover, an "anhydrous" form does not contain more than about 1% (w/w) of either water or organic solvents as measured for example by thermal gravimetric analysis (TGA).

The term "solvate", as used herein and unless indicated otherwise, refers to a crystal form that incorporates a solvent in the crystal structure. The solvent in a solvate may be present in either a stoichiometric or in a non-stoichiometric amount.

As used herein, the term "isolated" and unless indicated otherwise corresponds to escitalopram gentisate salt or solid state forms thereof that is physically separated from the reaction mixture in which it is formed.

The amount of solvent employed in a chemical process, e.g., a reaction or crystallization may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding methyl tert-butyl ether (MTBE) (1.5 v/v) to a 100 ml reaction mixture would indicate that 150 mL of MTBE was added.

As used herein the term "non-hygroscopic" in relation to a escitalopram gentisate, or a crystal form thereof, refers to less than about 1.0% (w/w) absorption of water at about 25° C. and about 80% relative humidity (RH) by escitalopram gentisate, or a crystal form thereof, as determined, for example, by TGA. Water can be, for example, atmospheric water.

As used herein, the term "reduced pressure" refers to a pressure of about 10 mbar to about 500 mbar.

As used herein, and unless indicated otherwise, the term "thermo-dynamical stability" in relation to escitalopram gentisate and its solid state forms refers to resistance of the solid state form to polymorphic conversion under certain conditions, for example, heating, melting or dissolving. In some embodiments, the term refers to less than about 20% (w/w), about 10% (w/w), about 5% (w/w), about 1% (w/w), about 0.5% (w/w), or about 0% (w/w) conversion of a crystal form of escitalopram gentisate to any other solid state form of escitalopram, or a salt thereof, as measured by XRPD. In some embodiments, the conversion is about 1% (w/w) to about 20% (w/w), about 1% (w/w) to about 10% (w/w), or about 1% (w/w) to about 5% (w/w).

Despite the large number of publications related to the chemistry of escitalopram, very little information on salt screening of escitalopram is available. US20040167209 discloses that a salt screening which involved more than 30 organic and inorganic acids and different solvent systems was not very successful, but provides no further details of the screening protocol. The study did not provide feasible solid salts, and all salts prepared appeared either as oil or amorphous solids having moderate to high hygroscopicity. An extensive salt study performed by the applicant of the present invention provides further support to the above findings.

Surprisingly, the applicant of the present invention managed to isolate and characterize a novel salt, escitalopram gentisate.

The currently known salts of escitalopram, escitalopram oxalate and escitalopram pamoate, are not suitable for various pharmaceutical composition. For example, the water solubility of escitalopram oxalate may be too high for some pharmaceutical compositions, while the water solubility of escitalopram pamoate may be too low.

Water solubility is often an important characteristic of an active pharmaceutical ingredient when formulating pharmaceutical compositions. Usually, when searching for a new salt the purpose is to increase solubility of the free base active compound by transforming it to a water soluble salt; in most cases, lower solubility is considered a disadvantage. The current invention addresses the need for a salt with an intermediate solubility, between the escitalopram pamoate and the escitalopram oxalate that is suitable for various pharmaceutical compositions other than those currently marketed.

The present invention relates to escitalopram gentisate and to solid state forms thereof, processes for preparation thereof, pharmaceutical compositions and formulations thereof.

In one embodiment, the present invention comprises escitalopram gentisate. The escitalopram gentisate may be isolated, preferably it is crystalline form.

In another embodiment, the present invention comprises a crystalline form of escitalopram gentisate designated as Form I. The crystalline Form I of escitalopram gentisate is characterized by data selected from one or more of the following: an XRPD pattern having peaks at 12.9; 16.8; 18.3; 19.9; and 21.1 degrees 2-theta±0.2 degrees 2-theta; an XRPD pattern substantially as depicted in FIG. 1 and/or FIG. 3; or combinations of thereof.

The crystalline Form I of escitalopram gentisate may be further characterized by an XRPD pattern having at least one of the following peaks at 9.2, 10.9, 15.9, 21.6, and 21.9 degrees two theta±0.2 degrees two theta.

Figure 2:
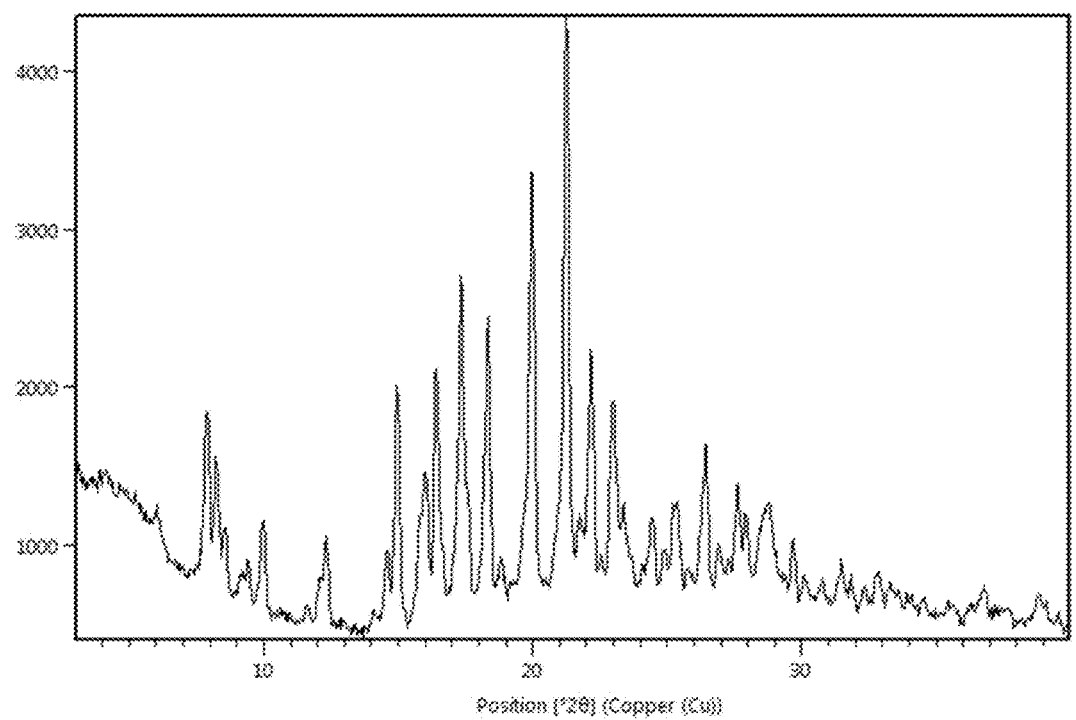
FIG. 2 shows an X-ray powder diffraction (XRPD) pattern of Form II of escitalopram gentisate prepared according to Example 4.

In yet another embodiment, the present invention further comprises a crystalline form of escitalopram gentisate designated as Form II. The crystalline Form II of escitalopram gentisate can be characterized by data selected from one or more of the following: an XRPD pattern having peaks at 10.0, 12.4, 17.3, 20.0; and 21.3, degrees two theta±0.2 degrees two theta; an XRPD pattern substantially as depicted in FIG. 2 and/or FIG. 4; or combinations thereof.

Crystalline Form II of escitalopram gentisate may be further characterized by an XRPD pattern having at least one of the following peaks at 8.0, 9.5; 15.0; 16.4; and 22.2 degrees two theta±0.2 degrees two theta.

The above described escitalopram gentisate, and solid state forms thereof, may be used to prepare other solid state forms of escitalopram gentisate and other escitalopram salts and their solid state forms thereof.

The present invention further encompasses processes for preparing said escitalopram gentisate, and solid state forms thereof. In some embodiments the staring material for the process is escitalopram base. In one embodiment the process comprises mixing escitalopram base with gentisic acid in an alcohol, for example isopropanol or methanol. In some embodiments the staring material is an escitalopram salt.

The present invention also encompasses the use of escitalopram gentisate, and solid state forms thereof, for the preparation of compositions and pharmaceutical compositions.

While the compounds for use according to the invention may be administered in the form of the raw compound, it is preferred to introduce the active ingredients in a pharmaceutical composition together with one or more adjuvants, excipients, carriers, buffers, diluents, and/or other customary pharmaceutical auxiliaries.

In one embodiment of the invention, the present invention encompasses pharmaceutical compositions comprising escitalopram gentisate and solid state forms thereof.

In another embodiment, the present invention encompasses pharmaceutical compositions comprising escitalopram gentisate, and solid state forms thereof, and at least one pharmaceutically acceptable excipient.

The excipient(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, (for example as tablet, capsule, dragé), and parenteral administration, in particular cutaneous, subcutaneous, intramuscular, or intravenous injection.

The pharmaceutical composition of the invention can be manufactured by the skilled person by use of standard methods and conventional techniques appropriate to the desired formulation.

The present invention further encompasses processes for preparing said pharmaceutical formulations comprising combining escitalopram gentisate, and solid state forms thereof, or pharmaceutical compositions comprising escitalopram gentisate, and at least one pharmaceutically acceptable excipient.

The salt and solid state forms thereof defined herein as well as the pharmaceutical compositions of the salt and solid state forms thereof, can be used as medicaments, preferably for the treatment of neuropsychiatric disorders, including major depressive disorder (MDD) and generalized anxiety disorder (GAD), comprising administering a therapeutically effective amount of escitalopram gentisate, or solid state forms thereof, to a subject suffering from neuropsychiatric disorders, more preferably major depressive disorder (MDD) or generalized anxiety disorder (GAD), or otherwise in need of treatment.

The present invention also provides the use escitalopram gentisate, and solid state forms, thereof for the manufacture of a medicament, preferably for treating neuropsychiatric disorders, more preferably major depressive disorder (MDD) or generalized anxiety disorder (GAD).

"Treatment" refers to the acute or prophylactic diminishment or alleviation of at least one symptom or characteristic associated or caused by a disorder being treated. In certain embodiments, treatment can include diminishment of several symptoms of a disorder or complete eradication of a disorder.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

EXAMPLES

Example 1: Analytical Methods

X-ray Powder diffraction ("XRPD") method: XRPD was performed on a PANalytical X'Pert Pro diffractometer equipped with an X'celerator detector using Cu Kα radiation at 45 kV and 40 mA. The diffractometer was controlled with PANalytical Data Collector1. All samples were analyzed using algorithms in HighScorePlus2. Scanning parameters: range: 2-40 degrees of two-theta; scan mode: continuous scan; step size: 0.0080°; counting time: 96.06 sec which resulted in a scan rate of ~0.5 deg/min.

Technical grade escitalopram base can be used as the starting material for the preparation of the gentisate salt. Material of commercial scale production was supplied by Huahai Zhejiang Pharmaceutical Co from Linhai Zhejiang, China, with assay 84%, Single impurity 0.53% (RT=24.38 min) and Total impurities 2.33%. Alternatively, escitalopram free base prepared from the oxalate salt, as described in Example 2, can also be used as the starting material. Gentisic acid is commercially available from Sigma Aldrich.

Example 2: Preparation of Escitalopram Base from Escitalopram Oxalate Salt

Escitalopram oxalate (40 g) and deionized water (170 ml) were introduced to a 250 ml jacketed glass reactor equipped with mechanical stirrer, circulating oil bath and thermometer. While the mixture was stirred, 45 ml of ether was added with the jacket temperature maintained at 25° C. throughout the isolation procedure. The pH of the mixture was adjusted to 9.0-9.5 by the addition of 25% $NH_4OH$. The stirrer was stopped to allow the settling of the mixture. Two liquid phases and solid precipitates formed. The resultant mixture was filtered and the obtained solid cake washed with 40 ml of ether. The filtrate and ether wash were then re-introduced into the reactor. Organic and aqueous phases were separated and collected into different containers. The aqueous phase was re-introduced to the reactor and extracted with 50 ml of ether. After settling, the aqueous phase was discarded. The two organic extracts were mixed in the reactor and washed twice with 25 ml of water. The organic solution was evaporated in a rotary evaporator under vacuum, with the bath temperature maintained at 70° C., until complete evaporation of solvent occurred. The resultant residue, 30.1 g of colorless clear oil (hot), was transferred to an amber glass vial.

Example 3: Preparation of Escitalopram Mono Gentisate Form I

Two hundred (200) microliter (μL) of 100 mg/mL clear solution of escitalopram free base (as described in example 2) in methanol was added to a 4 mL vial. The methanol was evaporated by uncovering the vial. The remaining material was dried at 60° C. and dried in a vacuum for 3 to 6 h after which 500 μL of 0.125M of gentisic acid in methanol was added to the vial. Methanol was again evaporated by uncovering the vial. The material was dried at 60° C. and further dried in a vacuum for 3 to 5 h. 250 μL of isopropanol was added to the dried material in the vial. A magnetic stirrer was placed into the vial and the mixture was stirred. Whenever the stirrer was stuck by the viscous material on the bottom of the vial, the solution was sonicated or the stirrer moved with a spatula. The vial was sonicated when whitish solids were identified as stuck to the side of the vial. Stirring continued for 24 to 28 hours by which time the solution had become a thick slurry. The slurry was filtered and the obtained solid was dried at 60° C. followed by vacuum drying overnight. The sample was subject to X-ray powder diffraction (XRPD) and identified as escitalopram gentisate form I. The XRPD pattern of escitalopram gentisate form I is shown in FIG. 1.

Example 4: Preparation of Escitalopram Mono Gentisate Form II

Four (4) mL of isopropanol, 300 mg of escitalopram free base (purified, example 2), and 148 mg of gentisic acid were added to a 20 mL vial and the mixture stirred with a magnetic stirrer. The mixture became clear and then a precipitate was observed. The solid material in the slurry was observed as being sticky. 5 mg of escitalopram mono gentisate, as prepared according to Example 3 was added to the mixture and stirred for an additional 2 hours. The resultant slurry was filtered and the obtained solids were dried at 60° C. and dried in a vacuum oven to obtain escitalopram mono gentisate. The sample was subject to XRPD, and identified as escitalopram gentisate form II. The XRPD pattern of escitalopram gentisate form II is shown in FIG. 2.

Figure 3:
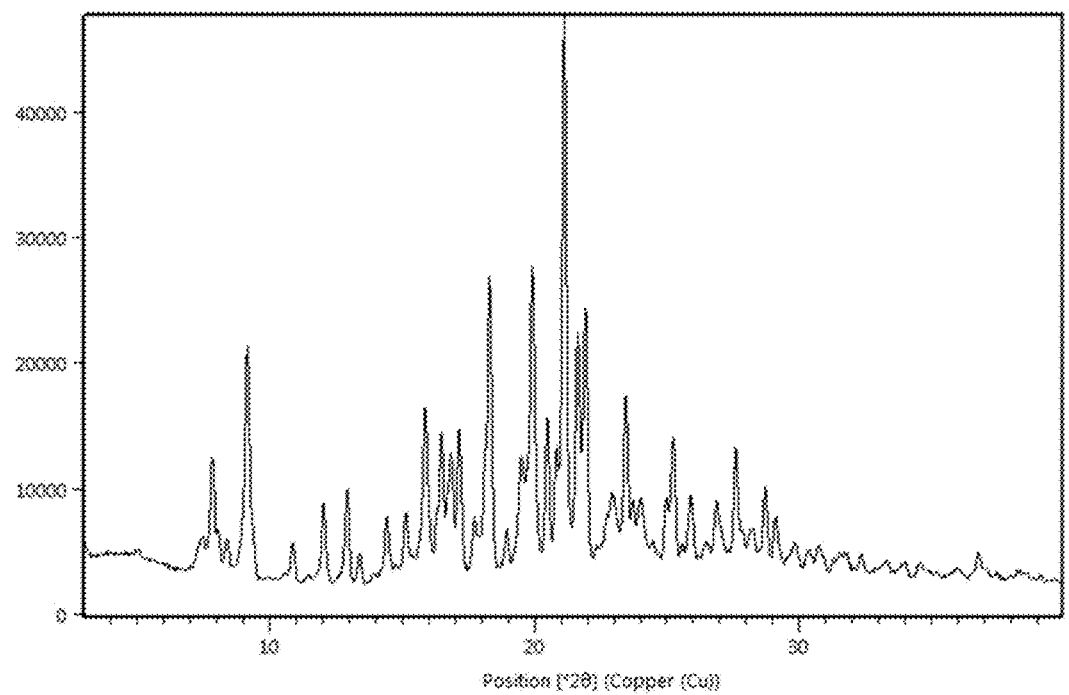
FIG. 3 shows an X-ray powder diffraction (XRPD) pattern of Form I of escitalopram gentisate prepared according to Example 5.

Example 5: Preparation of Escitalopram Mono Gentisate Form I 59.5 g of escitalopram free base (technical grade) was introduced to a 0.5 liter reactor together with 250 ml of isopropanol and stirred to reach complete dissolution. The reactor jacket temperature was adjusted to a Tj of 25° C. The resultant solution was seeded with crystals of escitalopram gentisate as prepared according to Example 4. A solution of 24.6 g of gentisic acid in 160 ml of isopropanol was added to the solution while stirring at a speed of 550 rpm for 7½ hrs. The solution was then stirred for an additional 2.5 hrs at Tj=25° C. and cooled to 18° C. for 4 hrs. The solution was filtered and the obtained solid cake was washed with 90 ml isopropanol and dried in a vacuum oven at 40° C. and 5 mbar to provide 69.0 g of a dry product, with a yield of 88.0%. The sample was subject to XRPD and identified as escitalopram gentisate form I. The XRPD pattern is shown in FIG. 3.

Figure 4:
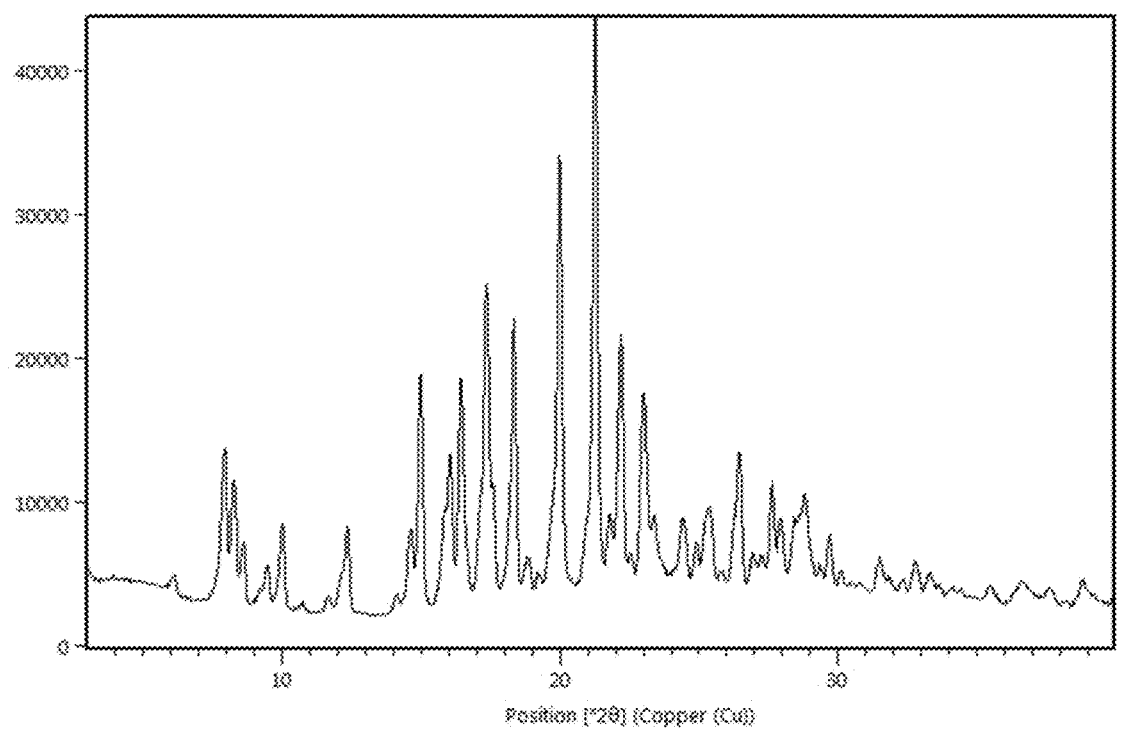
FIG. 4 shows an X-ray powder diffraction (XRPD) pattern of Form II of escitalopram gentisate prepared according to Example 6

Example 6: Preparation of Escitalopram Gentisate Form II 63.5 g of escitalopram gentisate, prepared according to Example 5, was introduced to a 0.5 liter reactor along with 560 ml isopropanol. The mixture was stirred and heated to 65° C. with the jacket temperature (Tj) maintained at 70° C. After the solids were dissolved, the Tj was adjusted to 50° C. While the solution temperature dropped to 47-48° C., crystals of escitalopram gentisate, as prepared according to Example 4, were added. The mixture was stirred at Tj=50° C. and 500 rpm for 8½ hrs, and then cooled to 18° C. for an additional 14 hrs. The resultant solid product was filtered, washed with 100 ml isopropanol and dried in vacuum oven at 40° C. and 5 mbar to provide 54.96 g of dry product, with a yield of 86.5%. The sample was subject to XRPD, and identified as escitalopram gentisate form II. The XRPD pattern is shown in FIG. 4.

The processes described in Examples 3-6 are scalable for commercial manufacture of escitalopram gentisate.

Example 7: Comparative Pharmacokinetics of Escitalopram Salts

Escitalopram salt solutions are prepared for intravenous (IV) and/or subcutaneous (SC) administration as follows: A 1 mg/kg solution of escitalopram oxalate (Ox-Esc) is prepared for IV administration at 1 mL/kg in 10% DMSO, 30% Solutol® (polyoxyethylated 12-hydroxystearic acid), 60% PBS.

A 1 mg/kg solution of escitalopram pamoate (P-Esc) is prepared for IV administration 1 mL/kg in 10% DMSO, 30% Solutol®, 60% PBS, and for SC administration 200 uL of 5 mg/kg in DMSO.

A 1 mg/kg solution of escitalopram gentisate (G-Esc) is prepared for IV administration 1 mL/kg in 10% DMSO, 30% Solutol®, 60% PBS, and for SC administration 200 uL of 5 mg/kg in DMSO.

Intravenous Pharmacokinetics of Escitalopram Oxalate

The pharmacokinetics of IV administered escitalopram oxalate are determined as follows. Sprague dawley rats (unfasted, 3 cohorts, 4-10 rats per cohort) are administered a single IV dose of escitalopram oxalate at 1 mg/kg in a dose volume of 1 mL/kg. Blood is collected from rats post dose in EDTA K2 tubes in a staggered design (cohort 1: 0 min, 30 min, 4 hr, 24 hr; cohort 2: 5 min, 1 hr, 8 hr, 36 hr; cohort 3: 15 min, 2 hr, 12 hr, 48 hr) and analyzed for escitalopram.

Intravenous and Subcutaneous Pharmacokinetics of Escitalopram Pamoate

The pharmacokinetics of IV administered escitalopram pamoate are determined as follows. Sprague dawley rats (unfasted, 3 cohorts, 4-10 rats per cohort) are administered a single IV dose of escitalopram pamoate at 1 mg/kg in a dose volume of 1 mL/kg. Blood is collected from rats post dose in EDTA K2 tubes in a staggered design (cohort 1: 0 min, 30 min, 4 hr, 24 hr; cohort 2: 5 min, 1 hr, 8 hr, 36 hr; cohort 3: 15 min, 2 hr, 12 hr, 48 hr) and analyzed for escitalopram.

The pharmacokinetics of SC administered escitalopram pamoate are determined as follows. Sprague dawley rats (unfasted, 3 cohorts, 4-10 rats per cohort) are administered a single SC dose of escitalopram pamoate at 5 mg/kg in a dose volume of 200 µl. Blood is collected from rats post dose in EDTA K2 tubes in a staggered design (cohort 1: 0 min, 1 hr, 8 hr, 48 hr; cohort 2: 5 min, 2 hr, 24 hr, 72 hr; cohort 3: 30 min, 4 hr, 36 hr, 96 hr) and analyzed for escitalopram.

Intravenous and Subcutaneous Pharmacokinetics of Escitalopram Gentisate

The pharmacokinetics of IV administered escitalopram gentisate are determined as follows. Sprague dawley rats (unfasted, 3 cohorts, 4-10 rats per cohort) are administered a single IV dose of escitalopram gentisate at 1 mg/kg in a dose volume of 1 mL/kg. Blood is collected from rats post dose in EDTA K2 tubes in a staggered design (cohort 1: 0 min, 30 min, 4 hr, 24 hr; cohort 2: 5 min, 1 hr, 8 hr, 36 hr; cohort 3: 15 min, 2 hr, 12 hr, 48 hr) and analyzed for escitalopram.

The pharmacokinetics of SC administered escitalopram gentisate are determined as follows. Sprague dawley rats (unfasted, 3 cohorts, 4-10 rats per cohort) are administered a single SC dose of escitalopram gentisate at 5 mg/kg in a dose volume of 200 µl. Blood is collected from rats post dose in EDTA K2 tubes in a staggered design (cohort 1: 0 min, 1 hr, 8 hr, 48 hr; cohort 2: 5 min, 2 hr, 24 hr, 72 hr; cohort 3: 30 min, 4 hr, 36 hr, 96 hr) and analyzed for escitalopram.

These pharmacokinetic data will demonstrate that the gentisate salt has a pharmacokinetic profile that will be distinct from those of the pamoate and oxalate salts. Escitalopram gentisate thereby fills the need for an escitalopram salt that is adaptable to pharmaceutical formulations for which the oxalate and pamoate salts are unsuitable.

Example 8. Treatment with Escitalopram Gentisate Composition

Periodically administering escitalopram gentisate to a human subject afflicted with a neuropsychiatric disorder provides a clinically meaningful advantage in reducing or eliminating the symptoms of the neuropsychiatric disorder. The therapy provides efficacy in treating the patient without undue adverse side effects or affecting the safety of the treatment. Periodic administration is meant to include inter alia IV, oral and subcutaneous administration. In some embodiments, the escitalopram gentisate is administered daily. In another embodiment, the escitalopram gentisate is administered more often than once daily. In another embodiment, the escitalopram gentisate is administered less often than once daily, for example every other day, three times a week, twice a week, once a week and the like.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the spirit and scope of the invention. All such similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications are herein incorporated by reference to the same extent as if each individual publication was specifically and individually indicated to be incorporated by reference.

REFERENCES

Elati, C R, et al. (2007) Substrate Modification Approach to Achieve Efficient Resolution: Didesmethylcitalopram: A Key Intermediate for Escitalopram. Organic Process Research & Development 11, 289-292

EP347066A1, New enantiomers and their isolation. Lundbeck A/S

US20040167209. Escitalopram hydrobromide and a method for the preparation thereof. Lundbeck A/S U.S. Pat. No. 7,723,533 Crystalline base of escitalopram and orodispersible tablets comprising escitalopram base. Lundbeck A/S

We claim:

1. A method of treating a neuropsychiatric disorder comprising parenterally administering to a subject in need thereof a therapeutically effective amount of escitalopram gentisate.

2. The method of claim 1, wherein the neuropsychiatric disorder comprises Major Depressive Disorder (MDD).

3. The method of claim 1, wherein the neuropsychiatric disorder comprises Generalized Anxiety Disorder (GAD).

4. The method of claim 1, wherein the parenteral administration is by injection.

5. The method of claim 4, wherein the parenteral administration is by cutaneous, subcutaneous, intramuscular or intravenous injection.

6. The method of claim 5, wherein the parenteral administration is by subcutaneous injection.

7. The method of claim 1, wherein the escitalopram gentisate is crystalline.

8. The method of claim 7, wherein the escitalopram gentisate is characterized by data selected from one or more of the following: an XRPD pattern having peaks at 12.9; 16.8; 18.3; 19.9; and 21.1 degrees 2-theta±0.2 degrees 2-theta; an XRPD pattern substantially as depicted in FIG. 1 and/or FIG. 3; or combinations of thereof.

9. The method of claim 8, wherein the escitalopram gentisate is further characterized by an XRPD pattern having at least one of the following peaks: 9.2, 10.9, 15.9, 21.6, and 21.9 degrees two theta±0.2 degrees two theta.

10. The method of claim 7, wherein the escitalopram gentisate is characterized by data selected from one or more of the following: an XRPD pattern having peaks at 10.0; 12.4, 17.3, 20.0, and 21.3 degrees two theta±0.2 degrees two theta; an XRPD pattern substantially as depicted in FIG. 2 and/or FIG. 4; or combinations thereof.

11. The method of claim 8, wherein the escitalopram gentisate is further characterized by an XRPD pattern having at least one of the following peaks: 8.0, 9.5, 15.0, 16.4, and 22.2 degrees two theta±0.2 degrees two theta.

12. A method of treating a neuropsychiatric disorder comprising parenterally administering to a subject in need thereof a pharmaceutical composition comprising a therapeutically effective amount of the escitalopram gentisate and a pharmaceutically acceptable excipient.

13. The method of claim 12, wherein the neuropsychiatric disorder comprises Major Depressive Disorder (MDD).

14. The method of claim 12, wherein the neuropsychiatric disorder comprises Generalized Anxiety Disorder (GAD).

15. The method of claim 12, wherein the pharmaceutical composition is formulated for injection into a subject in need thereof.

16. The method of claim 15, wherein the pharmaceutical composition is formulated for cutaneous, subcutaneous, intramuscular or intravenous injection into a subject in need thereof.

17. The method of claim 16, wherein the pharmaceutical composition is formulated for subcutaneous injection into a subject in need thereof.

18. A method of treating a neuropsychiatric disorder comprising subcutaneously administering to a subject in need thereof a therapeutically effective amount of escitalopram gentisate.

19. The method of claim 18, wherein the neuropsychiatric disorder comprises Major Depressive Disorder (MDD).

20. The method of claim 18, wherein the neuropsychiatric disorder comprises Generalized Anxiety Disorder (GAD).

* * * * *